United States Patent
Tornier

(10) Patent No.: US 7,608,075 B2
(45) Date of Patent: Oct. 27, 2009

(54) HUMERAL NAIL

(75) Inventor: Alain Tornier, Saint Ismier (FR)

(73) Assignee: Tornier SAS, Saint Ismier (FR)

( * ) Notice: Subject to any disclaimer, the term of this patent is extended or adjusted under 35 U.S.C. 154(b) by 277 days.

(21) Appl. No.: 11/340,615

(22) Filed: Jan. 27, 2006

(65) Prior Publication Data
US 2006/0173457 A1 Aug. 3, 2006

Related U.S. Application Data

(60) Provisional application No. 60/649,144, filed on Feb. 3, 2005.

(30) Foreign Application Priority Data
Feb. 1, 2005 (FR) ................................. 05 00986

(51) Int. Cl.
*A61B 17/56* (2006.01)
(52) U.S. Cl. ........................................... 606/64
(58) Field of Classification Search .............. 606/62, 606/64, 65, 66–68; 292/302; 70/229, 230, 70/232, 181; 411/522, 104, 922
See application file for complete search history.

(56) References Cited

U.S. PATENT DOCUMENTS

| | | | | |
|---|---|---|---|---|
| 4,622,959 A | * | 11/1986 | Marcus | 606/64 |
| 5,122,141 A | * | 6/1992 | Simpson et al. | 606/62 |
| 5,171,289 A | | 12/1992 | Tornier | |
| 5,314,485 A | | 5/1994 | Judet | |
| 5,326,359 A | | 7/1994 | Oudard | |

(Continued)

FOREIGN PATENT DOCUMENTS

| | | |
|---|---|---|
| JP | 200051225 | 9/2000 |
| WO | 2004/100810 | 11/2004 |

OTHER PUBLICATIONS

Rochetin, U.S. Appl. No. 11/194,452, entitled "Patellar Retractor and Method of Surgical Procedure on Knee," filed Aug. 2, 2005.

(Continued)

*Primary Examiner*—Eduardo C Robert
*Assistant Examiner*—Ellen Rust
(74) *Attorney, Agent, or Firm*—Faegre & Benson LLP

(57) ABSTRACT

A humeral nail includes an elongated body, a plurality of interlocking devices and a locking device. The elongated body is at least partially insertable into a medullary canal of a humerus and has a proximal part with a plurality of orifices. The interlocking devices are insertable into the orifices to interlock initially split humeral fragments. The locking device is capable of locking the interlocking devices within the orifices. The locking device is free to move relative to the body between a free passage position in which the locking device enables free passage of the interlocking devices through the orifices, and a locking position in which the locking device locks the interlocking devices in position with respect to the orifices. The locking device has a plurality of openings, each of which has a free passage portion in alignment with a corresponding orifice when the locking device is in the free passage position, and a locking portion in alignment with the corresponding orifice and in engagement with a corresponding interlocking device when the locking device is in the locking position.

22 Claims, 4 Drawing Sheets

U.S. PATENT DOCUMENTS

| | | | |
|---|---|---|---|
| 5,358,526 A | 10/1994 | Tornier | |
| 5,405,399 A | 4/1995 | Tornier | |
| 5,429,639 A | 7/1995 | Judet | |
| 5,458,650 A | 10/1995 | Carrett et al. | |
| 5,472,444 A | 12/1995 | Huebner | |
| 5,505,731 A | 4/1996 | Tornier | |
| 5,505,734 A * | 4/1996 | Caniggia et al. | 606/63 |
| 5,562,667 A * | 10/1996 | Shuler et al. | 606/64 |
| 5,591,168 A | 1/1997 | Judet et al. | |
| 5,653,709 A | 8/1997 | Frigg | |
| 5,658,287 A * | 8/1997 | Hofmann et al. | 606/63 |
| 5,662,651 A | 9/1997 | Tornier et al. | |
| 5,676,702 A | 10/1997 | Ratron | |
| 5,702,447 A | 12/1997 | Walch et al. | |
| 5,702,457 A | 12/1997 | Walch et al. | |
| 5,702,478 A | 12/1997 | Tornier | |
| 5,704,939 A * | 1/1998 | Justin | 606/63 |
| 5,766,256 A | 6/1998 | Oudard et al. | |
| 5,824,106 A | 10/1998 | Fournol | |
| 5,879,395 A | 3/1999 | Tornier et al. | |
| 5,928,235 A * | 7/1999 | Friedl | 606/64 |
| 6,120,504 A * | 9/2000 | Brumback et al. | 606/62 |
| 6,162,254 A | 12/2000 | Timoteo | |
| 6,165,224 A | 12/2000 | Tornier | |
| 6,168,595 B1 * | 1/2001 | Durham et al. | 606/64 |
| 6,168,629 B1 | 1/2001 | Timoteo | |
| 6,171,341 B1 | 1/2001 | Boileau et al. | |
| 6,183,519 B1 | 2/2001 | Bonnin et al. | |
| 6,206,925 B1 | 3/2001 | Tornier | |
| 6,228,086 B1 * | 5/2001 | Wahl et al. | 606/67 |
| 6,299,646 B1 | 10/2001 | Chambat et al. | |
| 6,328,758 B1 | 12/2001 | Tornier et al. | |
| 6,334,874 B1 | 1/2002 | Tornier et al. | |
| 6,379,387 B1 | 4/2002 | Tornier | |
| 6,402,753 B1 * | 6/2002 | Cole et al. | 606/62 |
| 6,454,809 B1 | 9/2002 | Tornier | |
| 6,488,712 B1 | 12/2002 | Tornier et al. | |
| 6,540,770 B1 | 4/2003 | Tornier et al. | |
| 6,582,469 B1 | 6/2003 | Tornier | |
| 6,599,295 B1 | 7/2003 | Tornier et al. | |
| 6,626,946 B1 | 9/2003 | Walch et al. | |
| 6,761,740 B2 | 7/2004 | Tornier | |
| 6,767,368 B2 | 7/2004 | Tornier | |
| 6,802,864 B2 | 10/2004 | Tornier | |
| 6,824,567 B2 | 11/2004 | Tornier et al. | |
| 6,890,357 B2 | 5/2005 | Tornier | |
| 6,921,400 B2 * | 7/2005 | Sohngen | 606/64 |
| 6,926,719 B2 * | 8/2005 | Sohngen et al. | 606/64 |
| 6,932,819 B2 * | 8/2005 | Wahl et al. | 606/67 |
| 6,969,406 B2 | 11/2005 | Tornier | |
| 7,018,380 B2 | 3/2006 | Cole | |
| 7,033,396 B2 | 4/2006 | Tornier | |
| 7,232,442 B2 * | 6/2007 | Sohngen et al. | 606/62 |
| 7,297,163 B2 * | 11/2007 | Huebner | 623/19.11 |
| 2003/0009170 A1 | 1/2003 | Tornier | |
| 2003/0009171 A1 | 1/2003 | Tornier | |
| 2003/0028198 A1 | 2/2003 | Tornier et al. | |
| 2004/0134821 A1 | 7/2004 | Tornier | |
| 2004/0210220 A1 | 10/2004 | Tornier | |
| 2004/0215200 A1 | 10/2004 | Tornier et al. | |
| 2004/0230197 A1 | 11/2004 | Tornier et al. | |
| 2005/0049709 A1 | 3/2005 | Tornier | |
| 2005/0055102 A1 | 3/2005 | Tornier et al. | |
| 2005/0165490 A1 | 7/2005 | Tornier | |
| 2005/0203536 A1 | 9/2005 | Laffargue et al. | |
| 2005/0278030 A1 | 12/2005 | Tornier et al. | |
| 2005/0278031 A1 | 12/2005 | Tornier et al. | |
| 2005/0278032 A1 | 12/2005 | Tornier et al. | |
| 2005/0278033 A1 | 12/2005 | Tornier et al. | |
| 2005/0288791 A1 | 12/2005 | Tornier et al. | |
| 2006/0015185 A1 | 1/2006 | Chambat et al. | |
| 2006/0064096 A1 * | 3/2006 | Prien | 606/64 |
| 2006/0095039 A1 * | 5/2006 | Mutchler | 606/64 |
| 2006/0235538 A1 | 10/2006 | Rochetin et al. | |
| 2007/0100343 A1 * | 5/2007 | Cole et al. | 606/67 |

OTHER PUBLICATIONS

Rochetin et al., U.S. Appl. No. 11/401,415, entitled "Surgical Apparatus for Implantation of a Partial or Total," filed Apr. 11, 2006.

Rochetin, U.S. Appl. No. 11/670,274, entitled "Offset Stem Tibial Implantation," filed Feb. 1, 2007.

Ratron et al., U.S. Appl. No. 11/626,735, entitled "Surgical Instrumentation Kit for Inserting an Ankle Prothesis," filed Jan. 24, 2007.

* cited by examiner

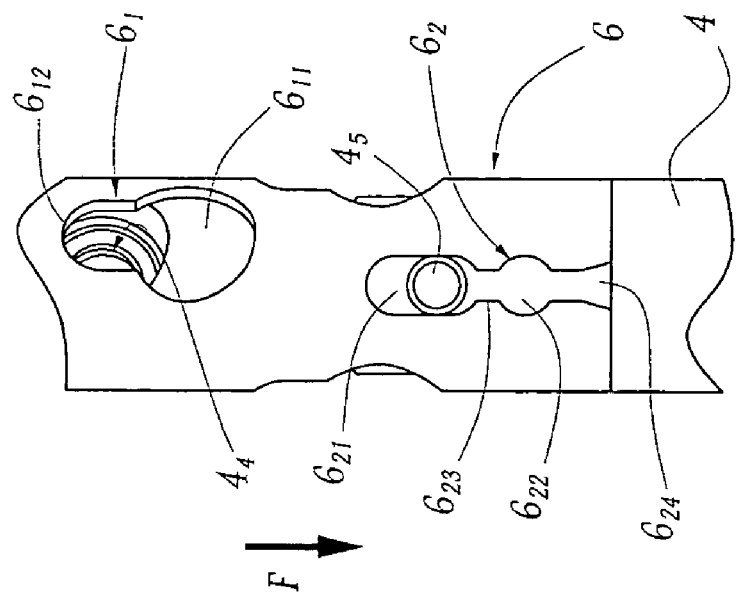
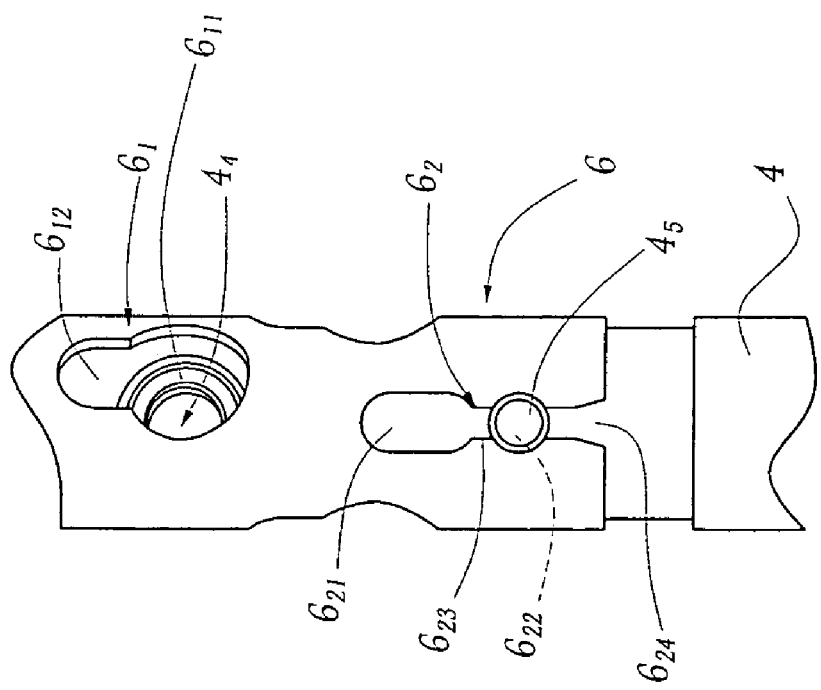

HUMERAL NAIL

This invention relates to a humeral nail.

When a fracture occurs, the proximal part of the humerus can break into several pieces. It is known that these different fragments can be brought together using a humeral nail like that according to the invention.

A nail of this type, for example like that disclosed in U.S. Pat. No. 5,472,444, includes an elongated body that is inserted in the medullary canal of the humerus. This body is hollowed out with various drillings through which screws can pass to mutually interlock the nail and the humeral shaft.

This body is terminated by a proximal end in which at least three orifices are formed, offset at angles from each other. These different orifices house corresponding screws that interlock the different bone fragments that were initially split.

However, this known solution has some disadvantages. Interlocking screws for bone segments tend to become unscrewed, such that their position is modified after implantation, which can cause pain for the patient. Furthermore, if this unscrewing takes place shortly after the surgical operation, consolidation of the humerus assembly may be completely deficient.

To overcome this disadvantage, WO-A-2004/100810 proposes a humeral nail with a main body, different interlocking screws and an internal sheath capable of sliding within the volume inside the body. This sheath has various orifices formed in it, through which the above-mentioned screws can pass.

The first step in placing the nail is to place the sheath inside the body of the nail, and then penetrate the screws through the various orifices formed in the body and in the sheath, respectively. The sheath is then moved along the main axis of the body so as to interlock the screws using the walls of the orifices in the sheath, which stop in contact with the surfaces facing the screws.

However, this alternate solution has disadvantages. In particular, the reliability of the attachment of the nail in the humerus is not always satisfactory.

Having said this, the invention is aimed at proposing a humeral nail capable of overcoming these various disadvantages.

Consequently, the present invention is a humeral nail including an elongated body that can be at least partially inserted into the medullary canal of the humerus, the body including a proximal part with housing orifices into which interlocking devices, such as screws, are inserted to interlock the initially split humeral fragments, the nail also includes a locking device capable of locking the interlocking devices, the locking device being free to move relative to the body between a position in which the interlocking devices are free to move, in which the locking device enables free passage of the interlocking means through the orifices, and a locking position of the interlocking devices in which the locking device locks the interlocking devices relative to the walls of the orifices, characterised in that the locking device includes several openings, each of which includes a free passage part extending in front of a corresponding orifice in the free passage position, and a locking part, the walls of which stop in contact with a corresponding interlocking device, in the locking position.

The invention will be better understood and other advantages will become more clear after reading the following description of an embodiment of a humeral nail according to its principle, given simply as a non-limitative example with reference to the attached drawings in which:

FIGS. 5 and 6 are elevations showing part of the body and the sheath forming part of the humeral nail in the previous figures in two different positions, at a different angle from that shown in FIGS. 2 and 3.

Figure 1:
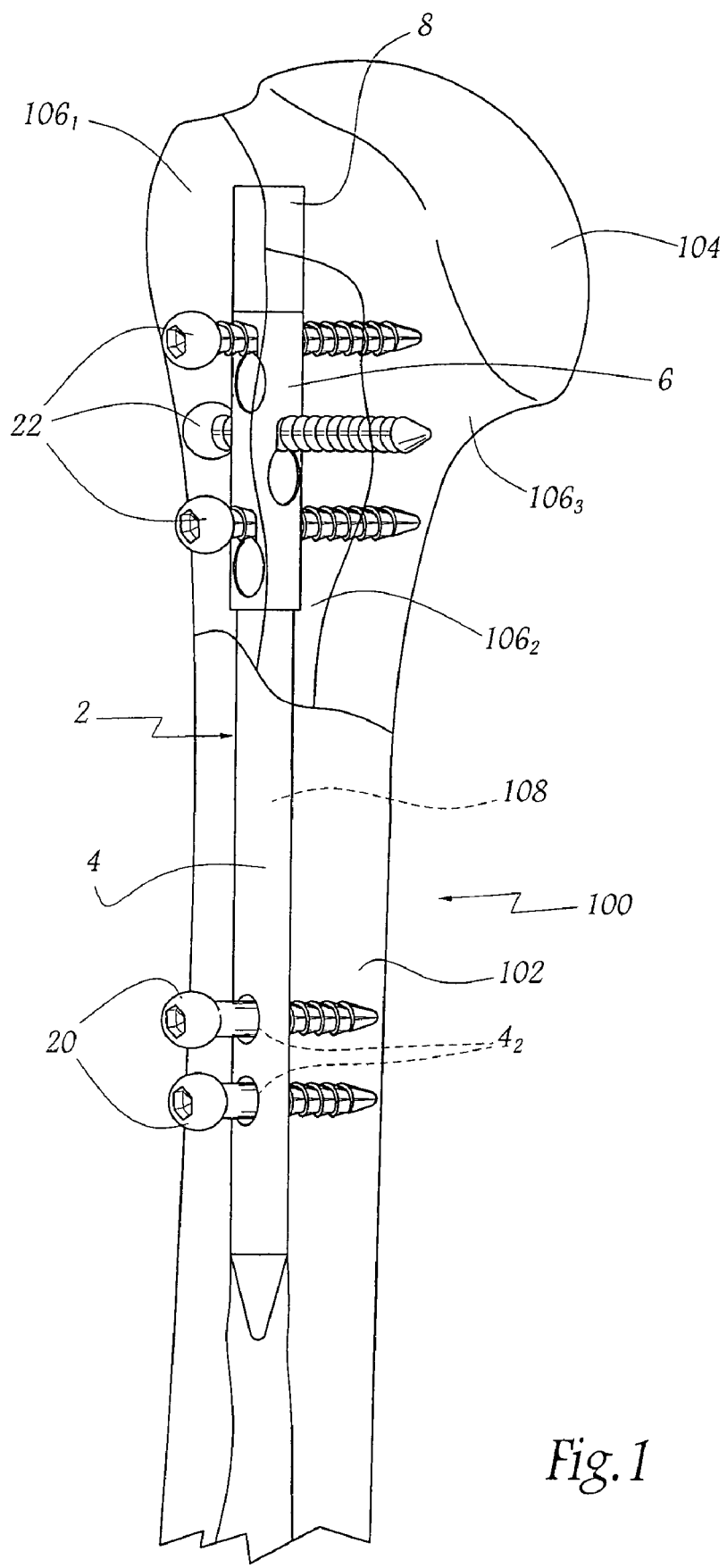
FIG. 1 is an elevation showing a humeral nail according to the invention, once implanted.

FIG. 1 shows a humeral nail according to the invention, denoted as a whole by reference $2$. The nail $2$ is used to consolidate a fracture that occurred at a humerus $100$ that includes a shaft $102$ and a head $104$. The initially split fragments $106_1$ to $106_3$ of the humerus $100$, for which the nail $2$ is used for consolidation, can also be seen in FIG. 1.

Figure 2:
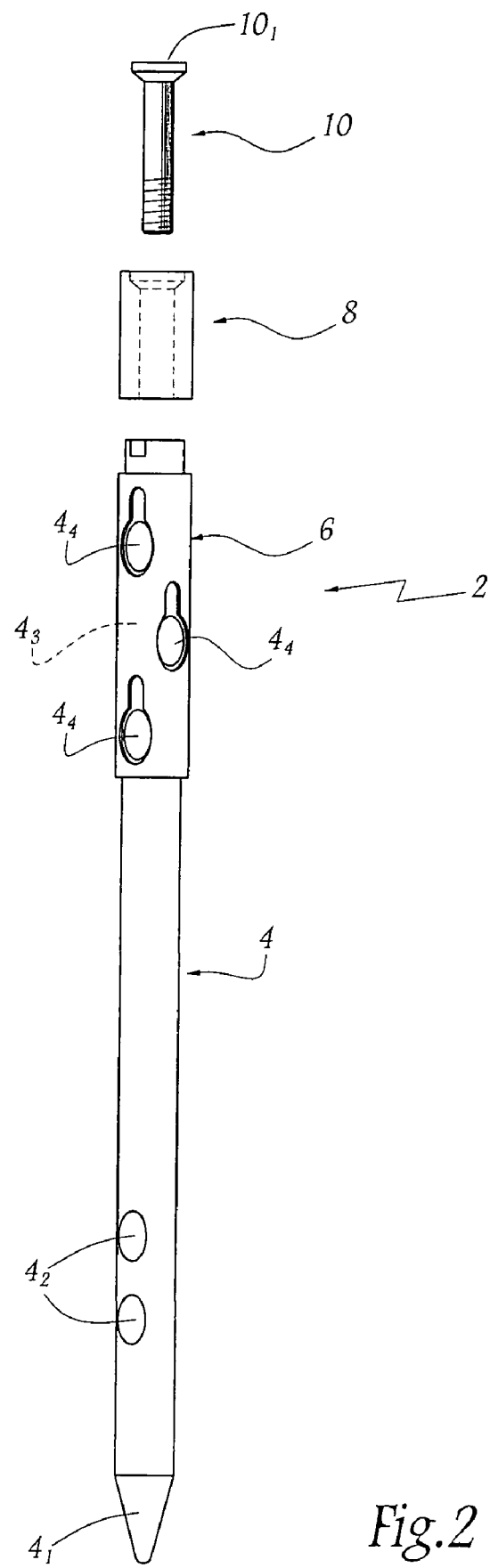
FIG. 2 is an exploded elevation showing two different constituents of the humeral nail in FIG. 1.

As shown particularly in FIG. 2, the nail $2$ includes an elongated body $4$ with a straight stem shape. The body $4$ is inserted into the medullar canal $108$ of the humerus and is provided with a tapered tip $4_1$ at its distal end. Furthermore, two through holes $4_2$ are formed in its median part, through which screws $20$ will pass. The screws $20$ interlock the body $4$ relative to the humeral shaft $102$ in a known manner.

The body $4$ is provided with a proximal part $4_3$ opposite the tip $4_1$ which is cylindrical in shape and has a circular cross-section. The proximal part is hollowed out with three through orifices $4_4$ that are circular in shape, and are arranged vertically in line with each other. The orifices $4_4$ may advantageously be offset at angles from each other in pairs according to the information given in U.S. Pat. No. 5,472,444.

Figure 3:
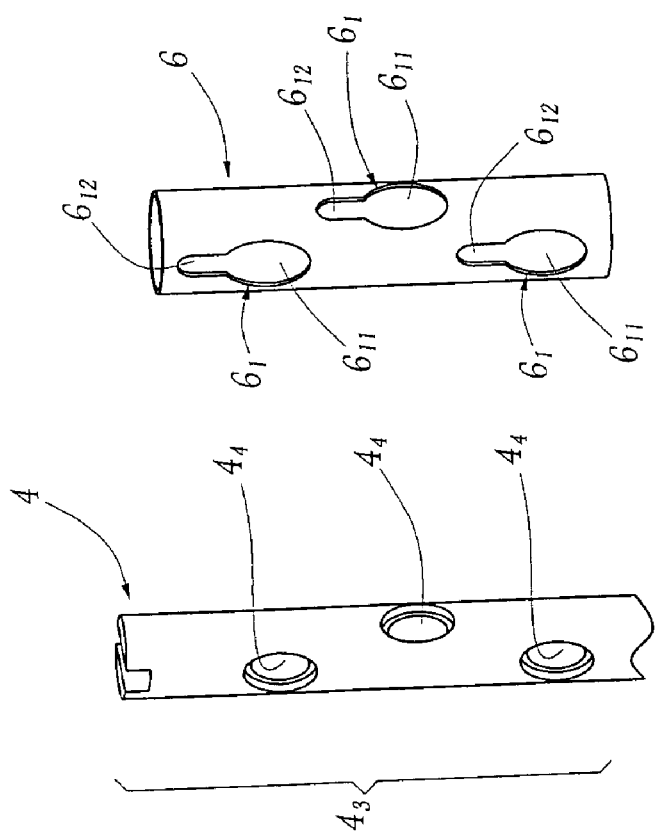
FIG. 3 is a larger scale elevation showing the orifices and openings in a body and a sheath respectively forming part of the humeral nail in the previous figures, side by side.

The humeral nail $2$ also includes a sheath $6$ open at both its ends that is visible particularly in FIG. 3. The sheath $6$ is cylindrical in shape and has a slightly greater diameter than the proximal part $4_3$ of the body $4$. Thus, the sheath $6$ is free to slide around the external surface of the proximal part $4_3$.

Three through openings $6_1$ pass through the sheath $6$, the locations of which correspond approximately to the locations of the orifices $4_4$. As shown more precisely in FIG. 3, which shows the orifices $4_4$ and the openings $6_1$ side by side, the openings $6_1$ have a circular part $6_{11}$, the diameter of which corresponds approximately to the diameter of the orifices $4_4$. The circular part $6_{11}$ is prolonged by an elongated slot $6_{12}$, the cross-section of which decreases towards the closed end (i.e. the upper end) of the slot $6_{12}$.

As shown particularly in FIGS. 5 and 6, the sheath $6$ is also hollowed out with a notch $6_2$ that opens up at its lower end, namely towards the tip $4_1$ of the body $4$. The notch $6_2$ defines two housings $6_{21}$ and $6_{22}$ that are oval and circular in shape, respectively, separated by a neck $6_{23}$ with a smaller through dimension. The lower circularly-shaped housing $6_{22}$ is prolonged by a canal $6_{24}$ opening up at the lower end of the sheath $6$.

Furthermore, the body $4$ is provided with a stud $4_5$ with a substantially circular section with through dimensions globally corresponding to the dimensions of the housings $6_{21}$ and $6_{22}$. As will be seen in the following, the stud $4_5$ can fit selectively into either of the two housings $6_{21}$ and $6_{22}$.

Finally, the humeral nail $2$ according to the invention comprises a hollow cylindrically-shaped cap $8$ with the same diameter as the sheath $6$. This cap $8$ can be blocked as will be seen in the following, using a screw $10$.

Placement of the nail $2$ in the humerus $100$ described above will now be explained in the following.

One objective is to add the sheath 6 around the proximal part $4_3$ so that the orifices $4_4$ coincide with the circular parts $6_{11}$ of the openings $6_1$. The assembly formed from the body 4 and the sheath 6 is then inserted into the medullary canal 108 of the humerus 100. As a variant, the body 4 can be inserted into the medullary canal 108 first, and the sheath 6 can then be added around the proximal part $4_3$. Furthermore, the stud $4_5$ of the body 4 fits into the lower housing $6_{22}$ of the notch $6_2$ formed in the sheath 6, which corresponds to the layout in FIG. 5.

Figure 4:
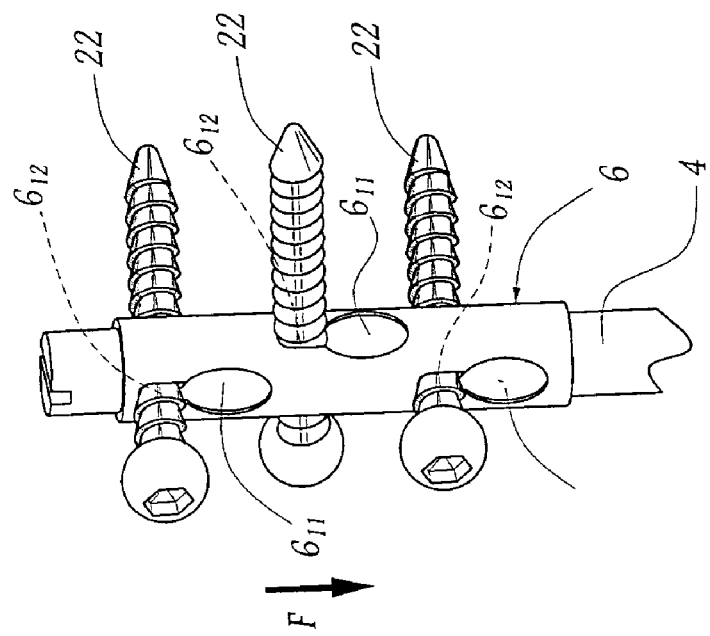
FIG. 4 is a perspective view showing an intermediate step in placement of a humeral nail represented in the previous figures.

Under these conditions, it is possible to pass interlocking screws 22 through the orifices $4_4$, the interlocking screws 22 being visible particularly in FIGS. 1 and 4. As is known particularly from U.S. Pat. No. 5,472,444, the screws 22 are used to interlock the initially fractured fragments $106_1$ to $106_3$, in order to consolidate them.

The sheath 6 is made to slide relative to the body 4 for example either manually or using an appropriate tool. In the example considered, the objective is to push the sheath 6 towards the distal part $4_1$ of the body 4, using the cap 8 and the screw 10.

More precisely, the cap 8 is added around the proximal part $4_3$ of the body 4, the screw 10 is inserted in the inner volume of the cap 8, and the screw 10 is then made to cooperate with an inner thread (not shown) formed in the proximal part $4_3$ of the body 4. This screwing of the screw 10 contributes to moving the cap 8 and consequently the sheath 6 along the main axis of the body 4, which is materialised by the arrow F in FIG. 4.

Therefore, it can be seen that the head $10_1$ of the screw 10 forms a stop for the cap 8 such that the cap 8 is immobilised axially relative to the body 4. Consequently, the cap 8 also contributes to axially locking the sheath 6 with respect to the body 4.

When the displacement mentioned above regarding the sheath 6 and the body 4 is terminated, the circular parts $6_{11}$ are no longer coincident with the orifices $4_4$, and the walls of the slots $6_{12}$ are then in contact with the surfaces facing the screws 22. The walls of the slots $6_{12}$ then act as a stop for the screws 22 and prevent any movement of the screws 22, particularly an unscrewing movement. The circular parts $6_{11}$ thus form free passage parts for the screws 22, while the slots $6_{12}$ form parts locking the screws 22.

It should be noted that the through dimensions of the circular parts $6_{11}$ are larger than the dimensions of the screws 22, such that the screws can slide freely. On the other hand, the through dimensions of the slots $6_{12}$ decrease towards the closed end of each slot. Consequently, when the sheath moves, the walls of these slots $6_{12}$ cap the surfaces facing the screws 22 so as to lock them and keep them in position.

Furthermore, sliding of the sheath 6 with respect to the body 4 causes displacement of the stud $4_5$ from the lower housing $6_{22}$ towards the upper housing $6_{21}$, which corresponds to the position in FIG. 6. It will be noted that this movement that takes place through the neck $6_{23}$ is enabled by the nature of the material from which the sheath 6 is made.

It can be imagined that in the position shown in FIG. 6, the sheath 6 is locked with respect to the body 4. The presence of the neck $6_{23}$ with a small through dimension prevents the stud $4_5$ from moving back towards the lower housing $6_{22}$, unless a large force is applied on the sheath 6. Consequently, this measure prevents any unexpected movement of the sheath 6 with respect to the body 4. It should be noted that the screws 22 are not shown in FIG. 6, for reasons of clarity.

The invention is not limited to the example described and shown.

The sheath 6 extending outside the body 4 can be replaced by a locking device installed free to slide inside the hollow body. The locking device has a smaller diameter and is also provided with openings through which the interlocking screws 22 can be selectively locked.

Furthermore, the slots can extend in different directions from the direction shown. Thus, they can extend the circular parts downwards, obliquely or laterally.

Furthermore, several types of sheaths can be used, the openings of which have different spacings and/or orientations. The most suitable sheath can be chosen for this purpose as a function of the configuration of the bone fragments to be brought together.

Finally, more than one locking notch can be provided to lock the sheath 6 with respect to the body 4, such as $6_2$ described with reference to FIGS. 5 and 6.

The invention provides a means of achieving the objective mentioned above.

The Applicant realised that the solution described in WO-A-2004/100810 is not very satisfactory, because it does not assure that the interlocking screws are reliably held in position. Thus, these screws are locked by the walls of circular orifices, which necessarily have a larger cross section than the screws since the screws need to slide through these orifices in the free passage position. Under these conditions, the locking force generated by the walls of these orifices is relatively low, such that the screws tend to move away from their initial position.

On the other hand, according to the invention, the sheath 6 reliably locks the interlocking screws 22 which prevents any accidental unscrewing. In this respect, it should be noted that the free passage part of each opening that has large dimensions enables easy sliding of the screws. Furthermore, the different locking parts that are smaller in dimension reliably hold these screws in position.

The invention claimed is:

1. A humeral nail for consolidating bone fragments of a humeral head, the humeral nail comprising:
    an elongated body adapted for insertion into a medullary canal of a humerus, the elongated body having a proximal part with a plurality of orifices and a stud;
    a plurality of screws insertable into the orifices to engage with, and to consolidate, the fragments of the humeral head;
    a hollow sheath comprising a notch sized to accept the stud and a plurality of openings which correspond approximately to locations of the plurality of orifices on the proximal part, the plurality of openings comprising a first portion with a diameter that corresponds approximately to a diameter of the orifices, and a second portion with a cross-section less than the diameter of the orifices; and
    the hollow sheath sized to freely slide axially along an external surface of the proximal part between a free passage position in which the first portions of the openings on the sheath are approximately aligned with the orifices on the proximal part, and a locking position in which the first portions of the openings on the hollow sheath are no longer coincident with the orifices on the proximal part and edges of the second portion of the openings contact surfaces on the screws, respectively.

2. The humeral nail of claim 1 wherein the screws comprise a threaded shaft and heads with diameters larger than the diameters of the orifices and adapted to turn freely in the orifices.

3. The humeral nail of claim 1 wherein the second portions of the openings on the hollow sheath comprise elongated slots.

4. The humeral nail of claim 1 wherein the second portions of the openings on the hollow sheath comprise cross-sections that decreases toward a closed end.

5. The humeral nail of claim 1 wherein the notch of the hollow sheath comprises a first housing positioned to engage with the stud on the proximal part when the hollow sheath is in the free passage position, and a second housing positioned to engage with the stud on the proximal part when the hollow sheath is in the locking position.

6. The humeral nail of claim 5 wherein the first and second housings comprise slots.

7. The humeral nail of claim 1 comprising a cap sized to engage with the external surface at a proximal end of the proximal part to advance the hollow sheath axially from the free passage position to the locking position.

8. The humeral nail of claim 1 comprising a threaded member that retains the hollow sheath in the locking position.

9. The humeral nail of claim 1 wherein the edges of the second portions of the openings comprise stops that prevent the screws from unscrewing.

10. The humeral nail of claim 1 wherein the second portions of the openings extend in one of a downward, oblique, or lateral direction relative to the first portions of the openings.

11. The humeral nail of claim 1 comprising:
a first hollow sheath with a plurality of openings in a first configuration; and
a second hollow sheath with a plurality of openings in a second configuration different from the first configuration, wherein the first and second hollow sheaths are selected as a function of the configuration of the bone fragments.

12. A method of consolidating bone fragments of a humeral head, the method comprising the steps of:
sliding a hollow sheath axially along an external surface of a proximal part of a humeral nail;
positioning the hollow sheath in a free passage position such that first portions of a plurality of openings on the hollow sheath correspond approximately with a plurality of orifices on the proximal part of the humeral nail, and second portions of the plurality of openings on the hollow sheath are at least partially offset from the orifices, wherein the first portions of the openings comprise diameters that corresponds approximately to diameters of the orifices, and the second portions with a cross-section less than the diameter of the orifices;
inserting the humeral nail into a medullary canal of a humerus;
aligning at least one of the orifices in the proximal part of the humeral nail with at least one bone fragment;
inserting at least one screw in one of the orifices;
engaging threads on at least one screw with at least one bone fragment of the humeral head;
rotating the screw to consolidate the bone fragment to the humeral head;
sliding the hollow sheath axially along the proximal part of the humeral nail to a locking position; and
engaging at least one edge of the second portions of the openings on the hollow sheath with the screw.

13. The method of claim 12 wherein the second portions of the openings on the hollow sheath comprise elongated slots.

14. The method of claim 12 wherein the second portions of the openings on the hollow sheath comprise cross-sections that decrease toward a closed end.

15. The method of claim 12 comprising the steps of:
engaging a first detent on the hollow sheath with a member on the humeral nail to retain the hollow sheath in the free passage position;
sliding the hollow sheath axially along the proximal part; and
engaging a second detent on the hollow sheath with the member to retain the hollow sheath in the locking position.

16. The method of claim 15 wherein the second detent comprises a slot.

17. The method of claim 12 comprising the step of engaging a cap with a proximal end of the proximal part to advance the hollow sheath from the free passage position to the locking position.

18. The method of claim 12 comprising retaining the hollow sheath in the locking position.

19. The method of claim 12 comprising orienting the second portions of the openings downward, obliquely, or laterally relative to the first portions of the openings.

20. The method of claim 12 comprising the steps of:
providing a first hollow sheath with a plurality of openings in a first configuration;
providing a second hollow sheath with a plurality of openings in a second configuration different from the first configuration; and
selecting the first and second hollow sheaths as a function of the configuration of the bone fragments.

21. A method of consolidating bone fragments of a humeral head, the method comprising:
sliding a hollow sheath axially along a surface of a proximal part of a humeral nail;
positioning the hollow sheath in a free passage position such that first portions of a plurality of openings on the hollow sheath correspond approximately with a plurality of orifices on the proximal part of the humeral nail, and second portions of the plurality of openings on the hollow sheath are at least partially offset from the orifices, wherein the first portions of the openings comprise diameters that corresponds approximately to diameters of the orifices, and the second portions with a cross-section less than the diameter of the orifices;
inserting the humeral nail into a medullary canal of a humerus;
aligning at least one of the orifices in the proximal part of the humeral nail with at least one bone fragment;
inserting at least one screw in one of the orifices;
engaging threads on at least one screw with at least one bone fragment of the humeral head;
rotating the screw to consolidate the bone fragment to the humeral head;
sliding the hollow sheath axially along the proximal part of the humeral nail to a locking position; and
engaging at least one edge of the second portions of the openings on the hollow sheath with the screw.

22. A method of consolidating bone fragments of a humeral head, the method comprising:
sliding a hollow sheath axially along a surface of a proximal part of a humeral nail;
positioning the hollow sheath in a free passage position such that first portions of a plurality of openings on the hollow sheath correspond approximately with a plurality of orifices on the proximal part of the humeral nail, and second portions of the plurality of openings on the hollow sheath are at least partially offset from the orifices, wherein the first portions of the openings comprise diameters that corresponds approximately to diameters of the orifices, and the second portions with a cross-section less than the diameter of the orifices;
inserting the humeral nail into a medullary canal of a humerus;
aligning at least one of the orifices in the proximal part of the humeral nail with at least one bone fragment;
inserting at least one screw in one of the orifices;
engaging threads on at least one screw with at least one bone fragment of the humeral head;
rotating the screw to consolidate the bone fragment to the humeral head;
rotating the hollow sheath around the humeral nail to a locking position; and
engaging at least one edge of the second portions of the openings on the hollow sheath with the screw.

* * * * *